US00PP34457P2

(12) United States Plant Patent
O'Connell

(10) Patent No.: US PP34,457 P2
(45) Date of Patent: Jul. 26, 2022

(54) ***PORTULACARIA* PLANT NAMED 'SNOWFALL'**

(50) Latin Name: *Portulacaria afra*
Varietal Denomination: 'SNOWFALL'

(71) Applicant: Altman Specialty Plants, Inc, Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/577,626

(22) Filed: Jan. 18, 2022

(51) Int. Cl.
*A01H 5/02* (2018.01)
*A01H 6/00* (2018.01)

(52) U.S. Cl.
USPC ..... Plt./471
CPC ..... *A01H 6/00* (2018.05)

(58) Field of Classification Search
USPC ..... Plt./471
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Portulacaria* plant named 'SNOWFALL' is disclosed, characterized by an overall small plant form and cascading morphology. Foliage is small, thickened, and colored variegated green and cream. Stems of the new variety are distinctively Greyed-Purple. The small size of the new variety makes it suitable for a variety of commercial pot sizes. Plants grow rapidly and begin offsetting early, enhancing propagation in the commercial nursery environment. The new variety is a *Portulacaria,* typically produced as a garden or container plant.

2 Drawing Sheets

Figure 1:
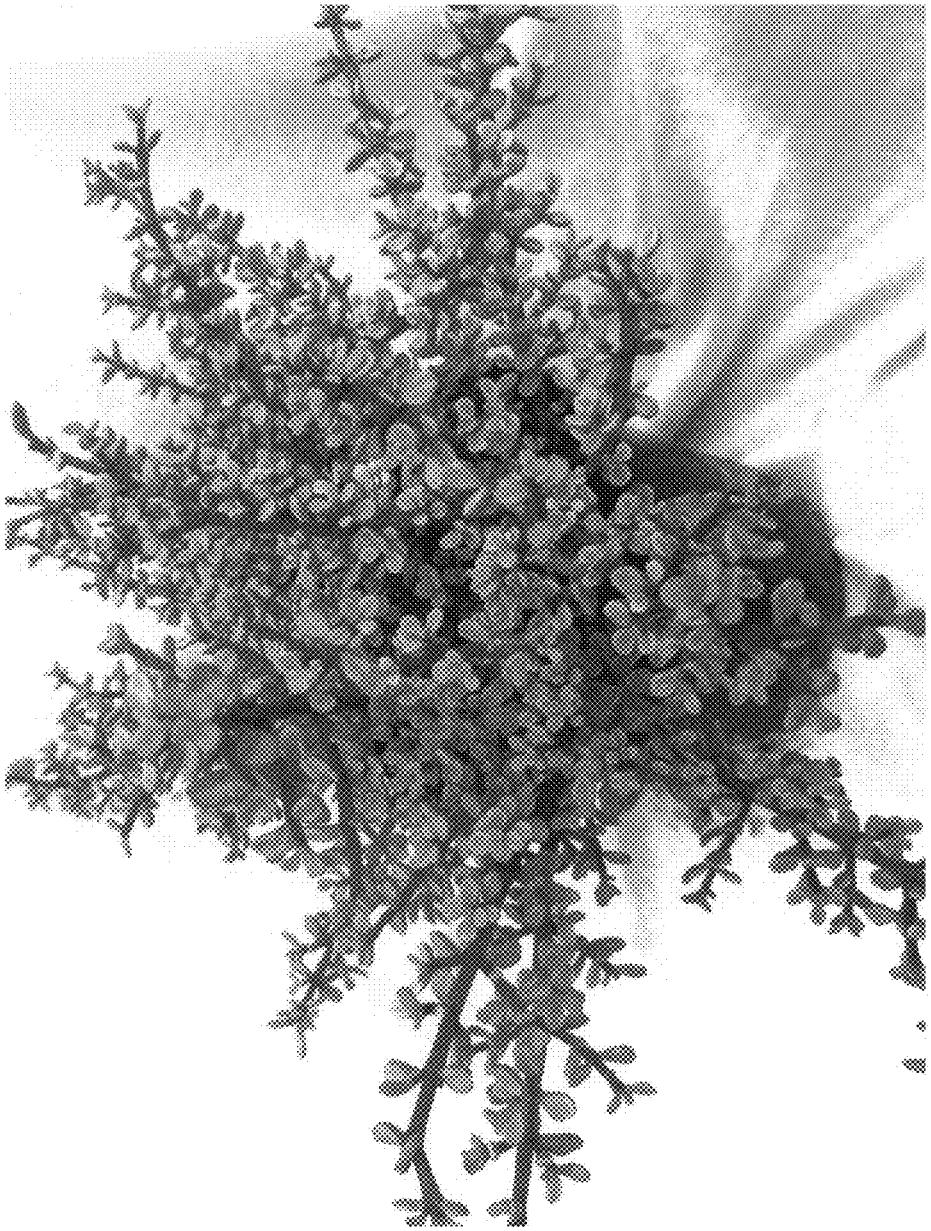

Latin name of the genus and species: *Portulacaria afra.* Variety denomination: 'SNOWFALL'.

BACKGROUND OF THE INVENTION

The new cultivar is a product of a naturally occurring whole plant mutation in a commercial nursery in Vista, Calif. The parent is the unpatented, variety of *Portulacaria afra*. 'Varigata' not patented. 'SNOWFALL' was found and selected by the inventor in Vista, Calif. in September of 2016.

Asexual reproduction of the new cultivar 'SNOWFALL' was first performed by vegetative tip cuttings at a commercial greenhouse in Vista, Calif. in October 2016. 'SNOWFALL' has since produced at least 15 generations and has shown that the unique features of this cultivar are stable and reproduced true to type.

SUMMARY OF THE INVENTION

The cultivar 'SNOWFALL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SNOWFALL.' These characteristics in combination distinguish 'SNOWFALL' as a new and distinct *Portulacaria* cultivar:

1. The new cultivar *Portulacaria afra* 'Snowfall' forms long, gracefully cascading greyed-purple branches densely covered in small green and creamy yellow variegated leaves.

2. Due to the cascading morphology of *Portulacaria afra* 'Snowfall', this plant is particularly adapted for hanging basket creations as well as accents in patio plantings.
3. *Portulacaria afra* 'Snowfall' begins to offset at an early age; resulting in an abundantly-branched morphology as well as a smaller plant. For this reason, and because of the more diminutive morphology, the cultivar *Portulacaria afra* 'Snowfall' can be utilized in a multitude of pot sizes, including smaller pot sizes.
4. As *Portulacaria afra* 'Snowfall' offsets heavily at a younger age, the result is the enhancement of propagation in a commercial nursery environment.

PARENTAL COMPARISON

Plants of the new cultivar 'SNOWFALL' are similar to the parent in most horticultural characteristics. However, plants of the new variety differ from the parent in the following:

1. *Portulacaria afra* 'Snowfall' exhibits a more diminutive morphology than does *Portulacaria afra* 'Variegate'.
2. *Portulacaria afra* 'Snowfall' exhibits thickened, chunky leaves, whereas *Portulacaria afra* 'Variegata' does not display thickened leaves.
3. *Portulacaria afra* 'Snowfall', due to its more compact morphology, can be utilized for smaller pot sizes, whereas *Portulacaria afra* 'Variegate' is more suited for larger pots.

COMMERCIAL COMPARISON

'Snowfall' can be compared to the commercial variety *Portulacaria afra* 'Manny' U.S. Plant Pat. No. 32,213. The two *Portulacaria* varieties are similar in most horticultural characteristics; however, the new variety differs in the following:

1. 'Snowfall' displays a more diminutive morphology than does *Portulacaria* 'Manny'.
2. 'Snowfall' displays a more cascading morphogy, suitable for a hanging basket, whereas *Portulacaria* 'Manny is a somewhat more upright plant.

'Snowfall' can also be compared to the commercial variety *Portulacaria afra* 'Lilliput', U.S. Plant Pat. No. 32,011. The two *Portulacaria* varieties are similar in most horticultural characteristics; however, the new variety differs in the following:

1. 'Snowfall' exhibits variegated leaves, whereas the leaves of *Portulacaria* 'Lilliput' are solid green, without variegation.
2. 'Snowfall exhibits chunky, thickened leaves, whereas *Portulacaria* 'Lilliput' does not display thickened leaves.
3. 'Snowfall' displays a graceful cascading morphology, ideal for hanging baskets, whereas *Portulacaria* 'Lilliput' exhibits a more upright morphology.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Portulacaria afra* 'Snowfall'.

FIG. 1 illustrates in full color a typical plant of of *Portulacaria afra* 'Snowfall', grown in a greenhouse (approximately 2500 foot candles) in Vista, Calif., at approximately 7 months.

Figure 2:
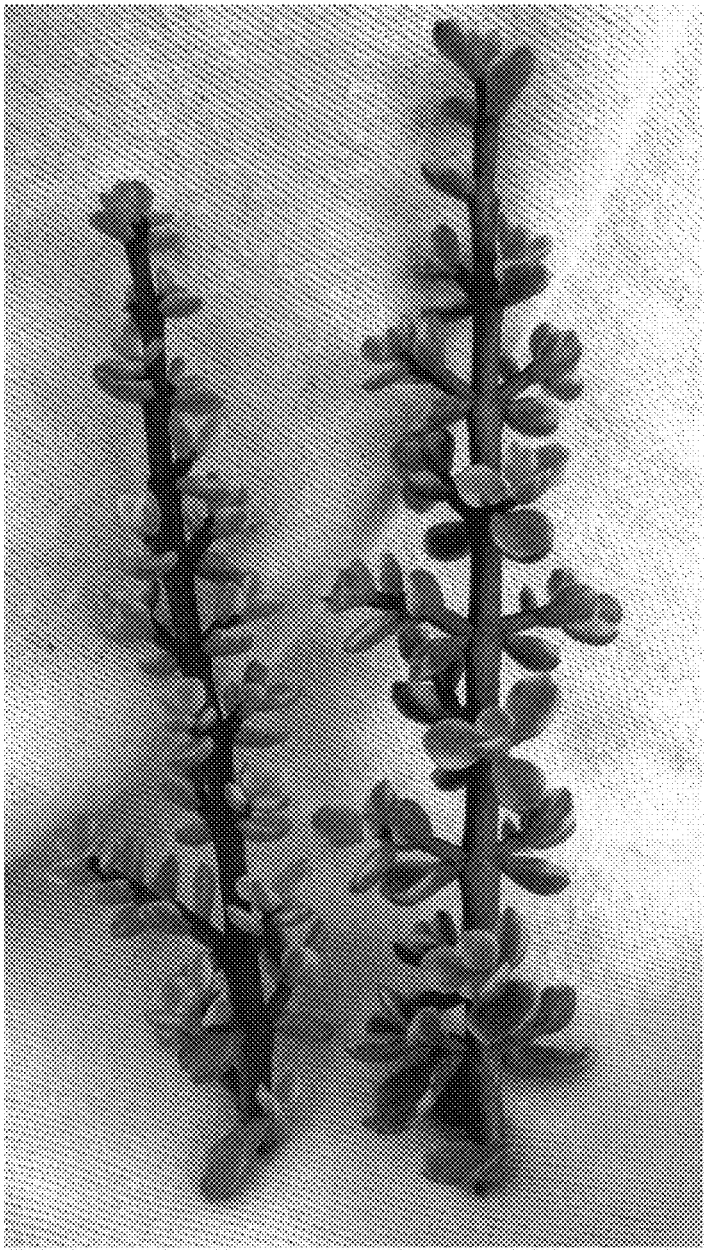

FIG. 2 illustrates in full color a comparison of stems and foliage of *Portulacaria afra* varieties. On the left is *Portulacaria afra* 'Snowfall'. On the right is *Portulacaria afra* 'Variegate'. Both plants were grown in a greenhouse (approximately 2500 foot candles) in Vista, Calif.

DETAILED BOTANICAL DESCRIPTION

In the following description, color references are made to The Royal Horticultural Society Color Chart, 2007 edition, except where general terms of ordinary dictionary significance are used. The following observations and measurements describe 'SNOWFALL' plants in a commercial shadehouse in Vista, Calif. Temperatures ranged from 34° F. to 90° F. during the night and day. No artificial light, photoperiodic treatments or chemical treatments were given to the plants. Natural light conditions were approximately 2500 to 3000 foot candles of light. Measurements and numerical values represent averages of typical plant types.

Botanical classification: *Portulacaria afra* 'SNOWFALL'.

Age of the Plant Described: About 6 months.

PROPAGATION

Time to initiate roots: Approximately 25 days at 22° C.

Propagation method: Vegetative tip cuttings.

PLANT

Growth habit: Tender succulent. Upright, with lateral branches occurring at obtuse angles, forming a cascading morphology.

Container size: 1 gallon.

Height: Approximately 18 cm.

Plant spread: Approximately 50 cm, in a 1-gallon pot.

Growth rate: Moderate.

Branching characteristics: Opposite. Each opposite pair occurring 90° from above pair.

Length of lateral branches: Main branches average 20 cm.

Diameter of lateral branches: Approximately 5 mm.

Quantity branches: 4 to 6 large main lateral branches, from each main stem. Upper section of main stems has 18 to 22 small lateral branches forming.

*Texture.*—Glabrous.

*Shape.*—Round.

*Color.*—Near RHS Greyed-Purple 187B.

Root description: Densely fibrous. Brown, not accurately measured with a standard color chart.

FOLIAGE

Leaf:

*Arrangement.*—Opposite, Sessile.

*Average length.*—Average range 9 to 11 mm.

*Average width.*—Average range 5 to 7 mm.

*Shape of blade.*—Obovate to broad spatulate.

*Apex.*—Broad acute to rounded.

*Base.*—Broad taper.

*Margin.*—Entire.

*Texture of top surface.*—Glabrous.

*Texture of bottom surface.*—Glabrous.

*Appearance of top surface.*—Matte.

*Appearance of lower surface.*—Matte.

*Quantity of leaves per branch.*—Approximately 120 to 180.

*Color.*—Young foliage upper side: Center near RHS Green 138B, fading to 138C. Margin near 150D. Newly emerging foliage flushed Greyed-Purple 187D. Young foliage, under side: Near RHS Green 138B, thin margin near Yellow-Green 145D. Mature foliage upper side: RHS Green 138C, margin near Yellow-Green 145D. Mature foliage, under side: RHS Green 138C.

*Venation.*—There is no visual appearance of venation.

FLOWER

Flowering not observed.

OTHER CHARACTERISTICS

Fruits and seeds: Not observed to date.

Temperature tolerance: USDA zones 10 and above.

Disease/pest resistance: Neither resistance nor susceptibility to standard pathogens or pests of *Portulacaria* observed.

Drought tolerance: Good tolerance for drought.

What is claimed is:

1. A new and distinct cultivar of *Portulacaria* plant named 'SNOWFALL' as herein illustrated and described.

* * * * *